United States Patent
Schwed et al.

(10) Patent No.: US 10,381,205 B1
(45) Date of Patent: Aug. 13, 2019

(54) MUON DRIFT TUBE AND METHOD OF MAKING SAME

(71) Applicant: Douglas Electrical Components, Inc., Randolph, NJ (US)

(72) Inventors: Stephen Schwed, Bridgewater, NJ (US); Edward William Douglas, Mendham, NJ (US); Stephen Diego Pellegrino, Randolph, NJ (US); Christopher Rempel, Morristown, NJ (US)

(73) Assignee: DOUGLAS ELECTRICAL COMPONENTS, INC., Randolph, NJ (US)

( * ) Notice: Subject to any disclaimer, the term of this patent is extended or adjusted under 35 U.S.C. 154(b) by 0 days.

(21) Appl. No.: 15/971,894

(22) Filed: May 4, 2018

(51) Int. Cl.
  H01J 47/00     (2006.01)
  G01T 1/18      (2006.01)
  G01N 23/04     (2018.01)
  G01T 1/185     (2006.01)
  G01N 23/046    (2018.01)

(52) U.S. Cl.
  CPC ............ H01J 47/008 (2013.01); G01T 1/185 (2013.01); H01J 47/001 (2013.01); G01N 23/046 (2013.01)

(58) Field of Classification Search
  CPC ............... H01J 37/02; H01J 37/252; H01J 47/001–47/008
  See application file for complete search history.

(56) References Cited

U.S. PATENT DOCUMENTS

| | | |
|---|---|---|
| 7,945,105 B1 | 5/2011 | Jaenisch |
| 8,274,377 B2 | 9/2012 | Smith et al. |
| 8,536,527 B2 | 9/2013 | Morris et al. |
| 8,939,909 B2 | 1/2015 | Wegner |
| 9,423,362 B2 | 8/2016 | Sossong et al. |
| 9,639,973 B2 | 5/2017 | Bai et al. |
| 9,784,859 B2 | 10/2017 | Blanpied et al. |
| 9,817,150 B2 | 11/2017 | Sossong |
| 9,841,530 B2 | 12/2017 | Blanpied et al. |
| 9,844,359 B2 | 12/2017 | Wegner |
| 9,851,311 B2 | 12/2017 | Sossong et al. |
| 2008/0315091 A1 | 12/2008 | Morris et al. |
| 2015/0212014 A1 | 7/2015 | Sossong et al. |
| 2015/0241593 A1 | 8/2015 | Blanpied et al. |
| 2015/0246244 A1 | 9/2015 | Sossong et al. |
| 2015/0325013 A1 | 11/2015 | Patnaik |
| 2016/0061752 A1 | 3/2016 | Kurnadi et al. |
| 2016/0097729 A1 | 4/2016 | Kurnadi et al. |
| 2016/0104290 A1 | 4/2016 | Patnaik |
| 2016/0116630 A1 | 4/2016 | Sossong |
| 2016/0231456 A1 | 8/2016 | McKenney et al. |

OTHER PUBLICATIONS

H. Kroha et al., New High-Precision Drift-Tube Detectors for the ATLAS Muon Spectrometer, arXiv:1705.05656v1 [physics.ins-det] May 16, 2017.

*Primary Examiner* — Michael C Bryant
(74) *Attorney, Agent, or Firm* — Weitzman Law Offices, LLC

(57) ABSTRACT

Various configurations of muon drift tubes for use in muon tomography are described and involve aluminum end caps coupled to an aluminum tube, an electrode in each of the end caps, and an anode wire extending between the electrodes. A two-part electrically conductive, gas-sealed, connection is located between an aluminum end cap and the aluminum tube. Methods of making those configurations of muon drift tubes are also described.

21 Claims, 12 Drawing Sheets

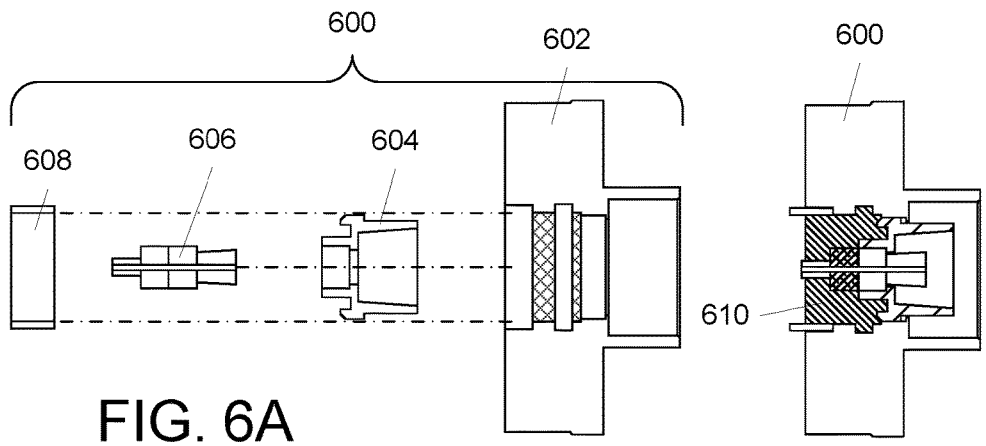
FIG. 6A
FIG. 6B
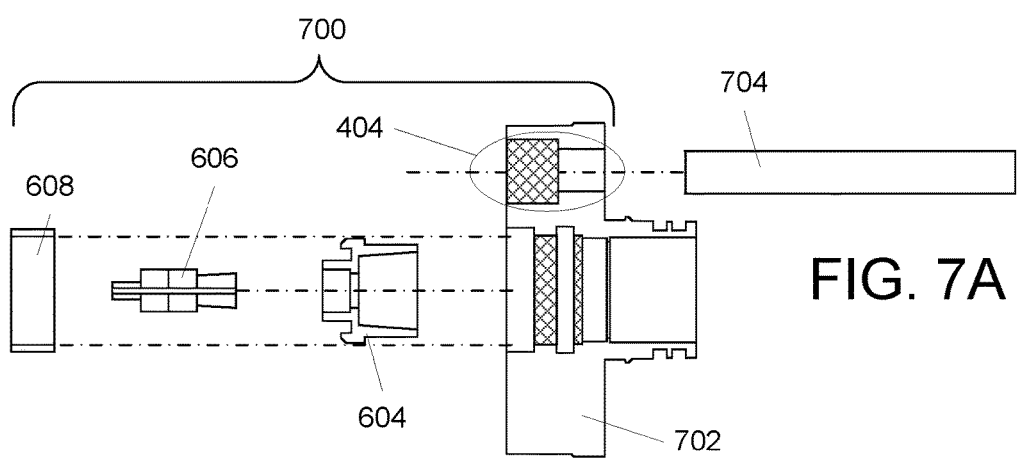
FIG. 7A
FIG. 7B
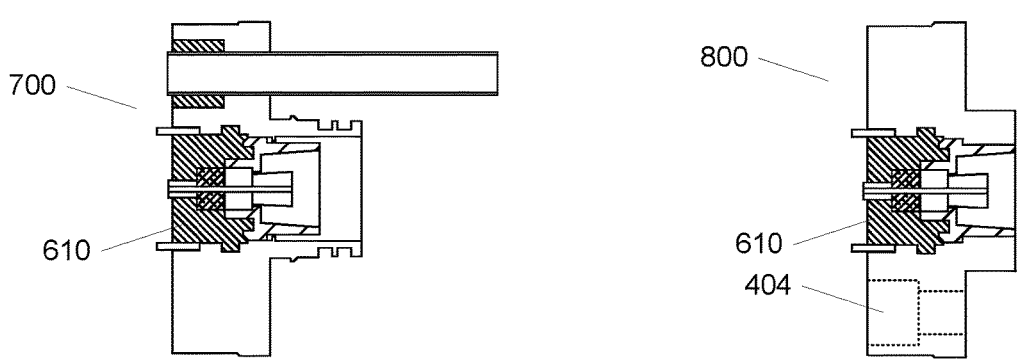
FIG. 8

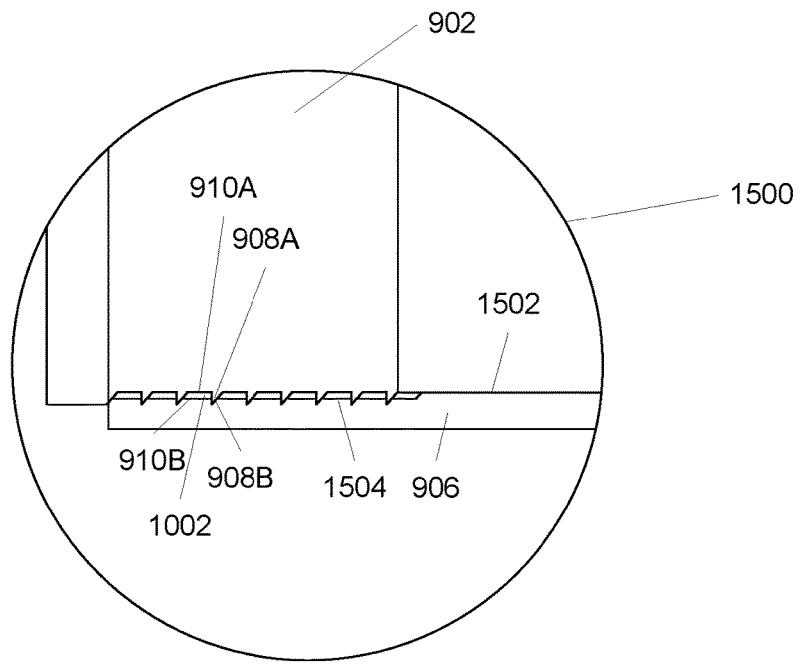
FIG. 15
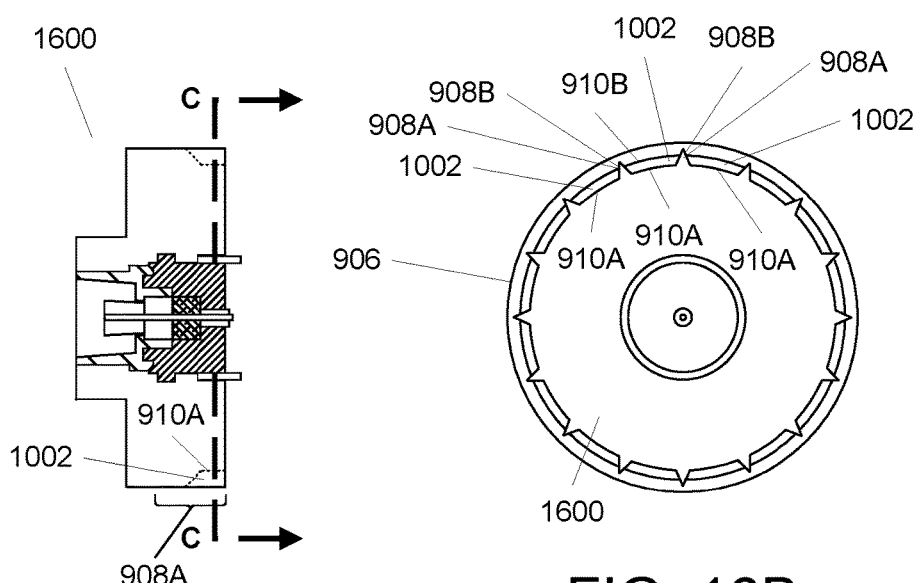
FIG. 16A
FIG. 16B

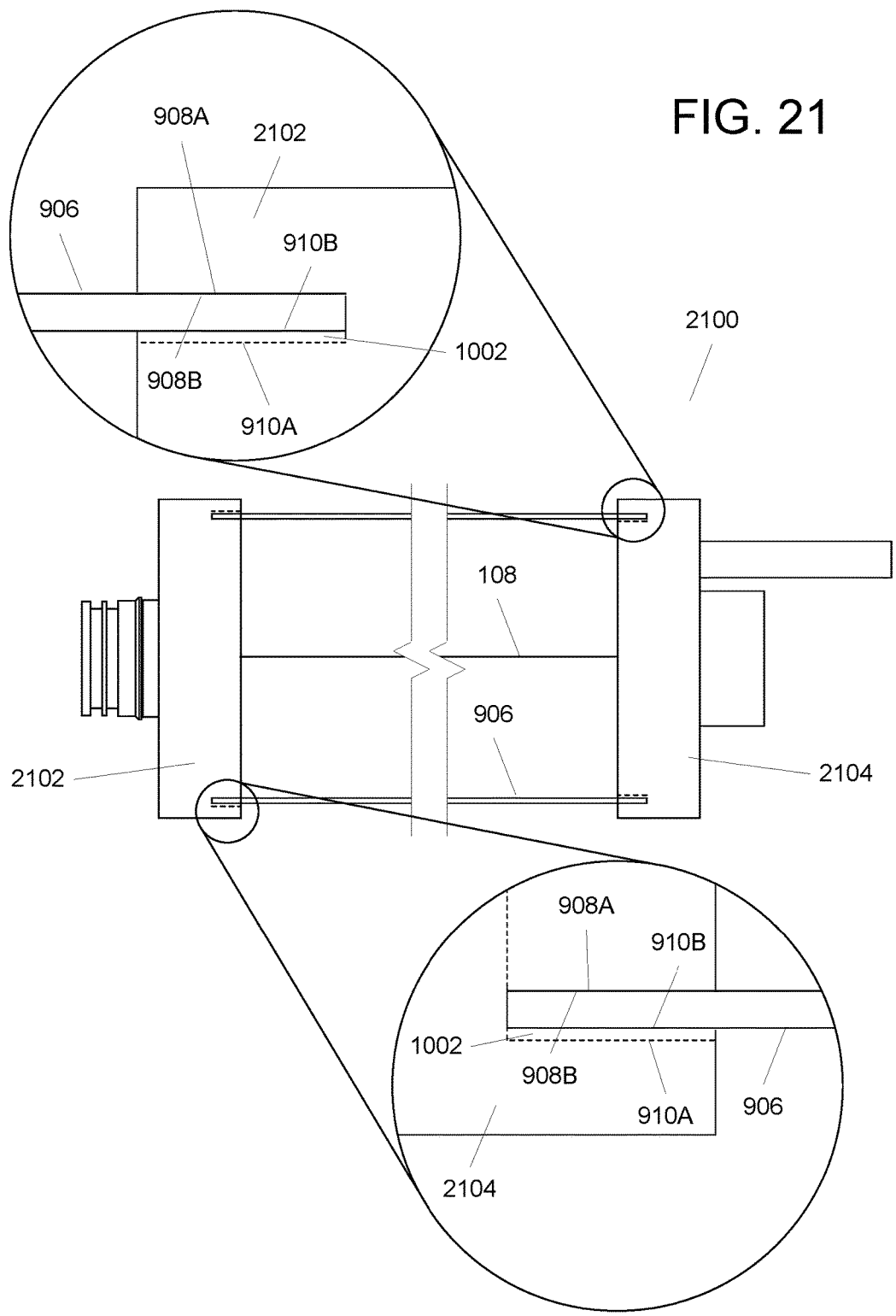

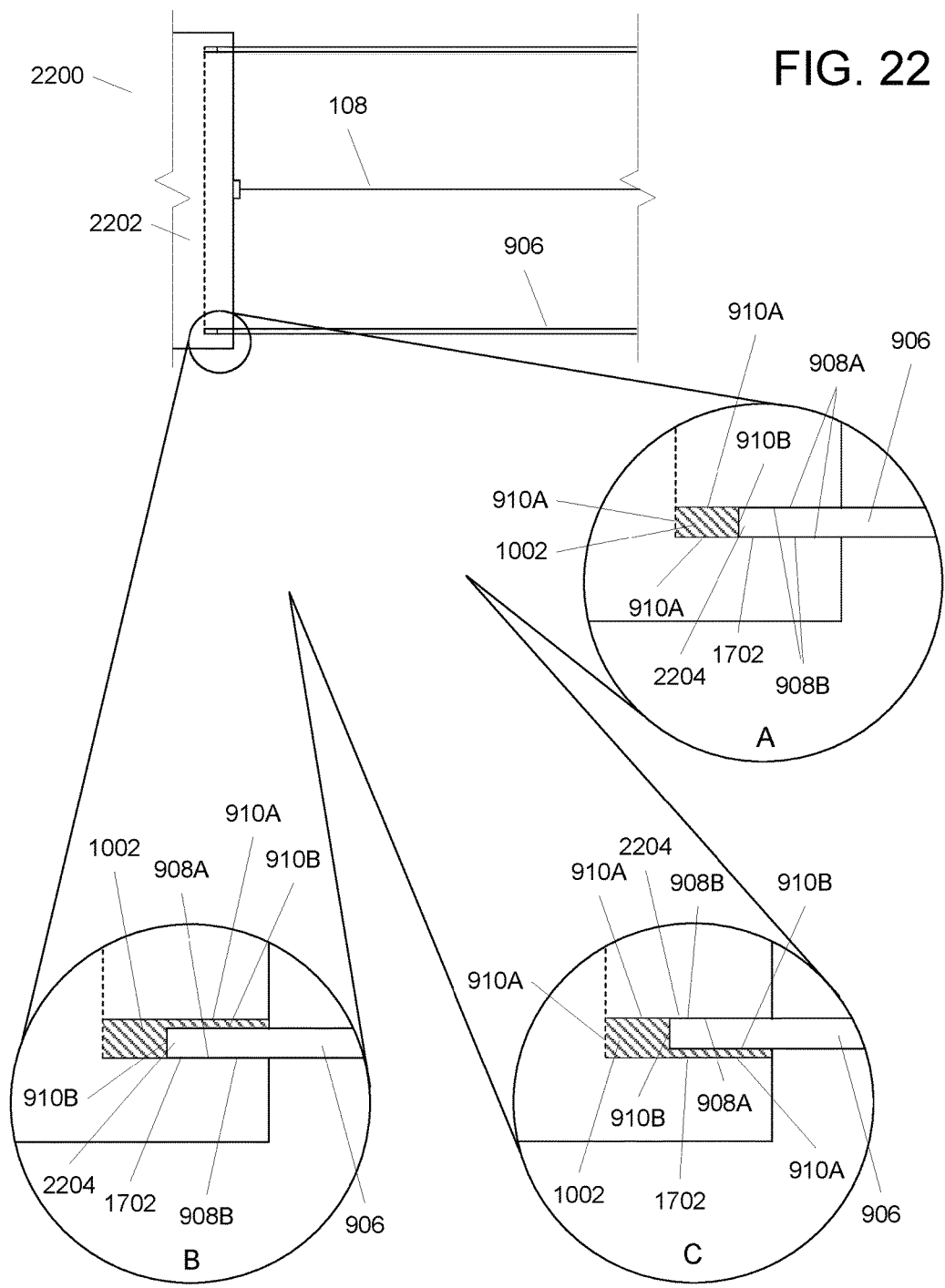

MUON DRIFT TUBE AND METHOD OF MAKING SAME

FIELD OF THE INVENTION

This disclosure relates generally to tomography and, more particularly, to drift tubes used in muon tomography.

BACKGROUND

Tomography is a process that uses penetrating waves to create an image. Muon tomography is a technique that uses muons to generate three-dimensional images of volumes based upon scattering of the muons as they pass muon drift tubes of a muon drift tube array.

A muon drift tube, of the type referred to herein, is basically a long cylindrical aluminum tube that is filled with a specific combination of gases, for example, $Ar:CO_2$ (93:7) or $Ar:C_2H_6:CF_4$ (49:7:44) and then sealed, and is designed to be sensitive to the passage of muons. The tube includes a thin wire, under tension, running through its center. In use, the wire acts as an anode and the aluminum tube acts as a cathode such that, when a high voltage is transmitted across the wire, electrons generated from a reaction between the muon and gas particles produce ions that will precipitate towards the wire. From this reaction, the drift time of the ionization electrons in the gas can be used to approximate the angle and position of the muon crossing the tube using a technique commonly referred to as "multiple-coulomb scattering."

There are multiple factors that affect the reliability, and consequently the performance of a drift tube. For example, temperature changes will cause the aluminum drift tube to expand and contract. The expansion and contraction, in turn, causes a change in the volume of the drift tube. As a result, an increase in temperature at constant pressure will result in both a lower gas density and higher drift velocity. Conversely, a decrease in temperature at constant pressure will result in both a higher gas density and lower drift velocity.

Muon drift tubes commonly have two specific causes of performance degradation and, ultimately, their failure—gas leakage and contamination.

In use, muon drift tubes are directly subject to temperature fluctuations. Moreover, it is not possible to create a perfect seal among the drift tube components that can remain intact through the in-use temperature fluctuations experienced by the muon drift tubes over a long period of time. As a result, gas leakage from a muon drift tube, over time, is a problem because it results in an inconsistency in the volume of gas within the muon drift tube over time. Moreover, it is a greater problem when a mixture of gases is used, because the gases will have different leakage rates due to their different densities, causing a change in the mixture itself.

Another source of degradation and failure is contamination of the gas mixture by infiltration of contaminants, such as water, air and hydrogen. Contaminant infiltration affects, among other things, the electron drift time over time. Moreover, compensating for contamination is very difficult because it a variable that is often a function of the physical environment at the specific drift tube location.

To ensure that the muon drift tubes have sufficient life and reliability over time, the joint between the tubes and end caps must be sealed, at manufacture, to a Helium gas leak rate of less than $1 \times 10^{-8}$ bar l/s as measured by a mass spectrometer leak detector.

Meeting this requirement requires the use of multiple special component parts and incorporation of special, complex features into the components, and the manufacture further involves the use of complex, laser welding or crimping equipment that is expensive to acquire and maintain. Still further, the manufacture must be performed by well-trained/experienced operators/engineers. All of the foregoing leads to a high manufacturing cost.

Thus, there is a need in the art for a simpler, less expensive way to produce those muon drift tubes, that can nevertheless meet the current, stringent, hermeticity requirements.

SUMMARY

We have devised a solution to the foregoing problems. More particularly, we have devised a muon drift tube configuration, and method of its manufacture, to address one or more of the foregoing problems by providing a simplified configuration and approach that, for example, can eliminate components and/or the need for high precision laser welding equipment, and/or can improve manufacturability. in terms of cost, experience and/or time.

One aspect of this disclosure involves a muon drift tube for use in muon tomography. The muon drift tube is made up of an aluminum tube having a first end, a second end, and a longitudinal axis, an aluminum first cap coupled to the first end of the tube, an aluminum second cap coupled to the second end of the tube, a first electrode physically coupled to, but electrically isolated from, the first cap, a second electrode physically coupled to, but electrically isolated from, the second cap, and a conductive wire within the tube extending, along the longitudinal axis, between the first electrode and the second electrode.

The first cap and the first end of the tube are coupled to each other so as to form an electrically conductive, gas-sealed connection between them, the connection including: a) interference-fit-based galling between a first segment of the first end of the aluminum tube and a corresponding first segment of the first cap, and b) a high elongation polymer, located between a second segment of the aluminum tube and a corresponding second segment of the first cap.

A thickness of the high elongation polymer, measured radially, normal to a surface of the tube at the second segment of the connection, is less than 500 micrometers.

Another aspect of this disclosure involves a muon drift tube for use in muon tomography. The muon drift tube is made up of an aluminum tube having a first end, a second end, and a longitudinal axis, an aluminum first cap coupled to the first end of the tube, an aluminum second cap coupled to the second end of the tube, a first electrode physically coupled to, but electrically isolated from, the first cap, a second electrode physically coupled to, but electrically isolated from, the second cap, and a conductive wire within the tube extending, along the longitudinal axis, between the first electrode and the second electrode.

A first segment of the first end of the aluminum tube and a first segment of the first cap are interference-fit together so as to form an electrically conductive path between them.

A second segment of the first end of the aluminum tube and a corresponding second segment of the first cap are spaced apart from each other so as to form a gap between them of greater than 125 micrometers.

A high elongation polymer, bonded to at least one of the aluminum tube or first cap, is located within the gap, so that, the first segments and second segments will collectively form an electrically conductive, gas-sealed, connection between the first end cap and the aluminum tube.

Yet another aspect of this disclosure involves a method of making a muon drift tube for use in muon tomography. The method involves i) threading an anode wire through an aluminum tube having a first end, a second end, and a longitudinal axis, such that the wire extends beyond both the first end and second end of the aluminum tube; ii) inserting a first end of the anode wire into a first electrode located within, but electrically isolated from, a first end cap; iii) inserting a second end of the anode wire into a second electrode located within, but electrically isolated from, a second end cap; iv) coupling a first part of the first end cap to the first end of the aluminum tube, and coupling a first part of the second end cap to the second end of the aluminum tube; v) tensioning the anode wire such that the longitudinal axis of the aluminum tube and the anode wire are co-linear; and vi) coupling portions of the tensioned anode wire, associated with the first and second ends of the tensioned anode wire, to the first and second electrodes.

In addition, with respect to coupling the first end cap to the aluminum tube, a second segment of one of the first part of the first end cap, or a second segment of the first end of the aluminum tube, includes a high elongation polymer, and a first segment of both the first part of the first end cap and a first segment of the second end of the aluminum tube are substantially free of the high elongation polymer.

The coupling of the first part of the first end cap to the one end of the aluminum tube in "iv)" further involves interference fitting the first part of the first end cap and the first end of the aluminum tube together such that galling will occur between the respective first segments.

The method further includes forming a flexible seal between the respective second segments and, such that the first and second segments collectively form an electrically conductive, gas-sealed, connection between the first end cap and the aluminum tube.

The foregoing and following outlines rather generally the features and technical advantages of one or more embodiments of this disclosure in order that the following detailed description may be better understood. Additional features and advantages of this disclosure will be described hereinafter, which may form the subject of the claims of this application.

BRIEF DESCRIPTION OF THE DRAWINGS

This disclosure is further described in the detailed description that follows, with reference to the drawings, wherein the same reference numerals refer to the same parts throughout the various views, in which:

FIG. 6A illustrates, in simplified form, an exploded, cross sectional, view of the components of one example variant "female" style end cap for use in constructing a muon drift tube;

FIG. 6B illustrates, in simplified form, a cross sectional, view of the assembled example variant "female" style end cap of FIG. 6A;

FIG. 7A illustrates, in simplified form, an exploded, cross sectional, view of the components of an alternative example variant end cap for use in constructing a muon drift tube;

FIG. 7B illustrates, in simplified form, a cross sectional, view of the assembled example variant "male" style end cap of FIG. 7A;

FIG. 8 illustrates, in simplified form, a cross sectional, view of an assembled example variant aluminum end cap that is a "generic" style;

FIG. 9 illustrates, in simplified form, one example variant of our approach to sealing an aluminum end cap to an aluminum tube during formation of a muon drift tube so as to form an electrically conductive, gas-sealed connection between;

FIG. 15 illustrates, in simplified form, an additional enlarged cross section cutaway portion of yet another alternative variant muon drift tube having an electrically conductive, gas-sealed connection between an aluminum end cap and aluminum tube;

FIG. 16A illustrates, in simplified form, a cross section of a further alternative variant aluminum end cap for use in constructing a muon drift tube having an electrically conductive, gas-sealed connection between an aluminum end cap and aluminum tube;

FIG. 16B illustrates, in simplified form, a cross section of the aluminum end cap as it would look after insertion into an aluminum tube;

FIG. 21 illustrates, in simplified form, alternative end portions of a muon drift tube constructed according to the teachings herein in order to form an electrically conductive, gas-sealed connection between an aluminum end cap and aluminum tube using an end cap having a groove as described in connection with FIG. 17A; and FIG. 22 illustrates, in simplified form, enlargements of cross sections of alternative end portions of a muon drift tube that was constructed according to the teachings herein in order to form an electrically conductive, gas-sealed connection between an aluminum end cap and aluminum tube.

DETAILED DESCRIPTION

Our technical solution improves upon current technology and provides a solution to aforementioned problems.

Figure 1:
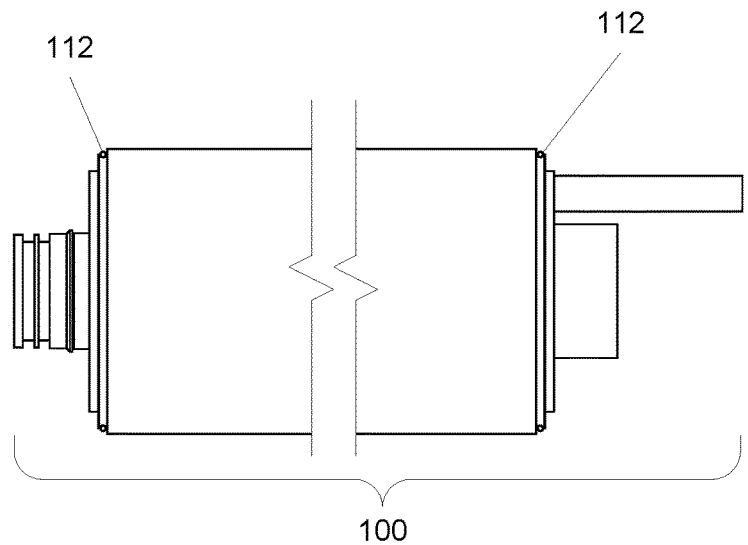
FIG. 1 illustrates, in simplified form, ends of one example assembled conventional muon drift tube.

FIG. 1 illustrates, in simplified form, ends of one example assembled conventional muon drift tube 100.

Figure 2:
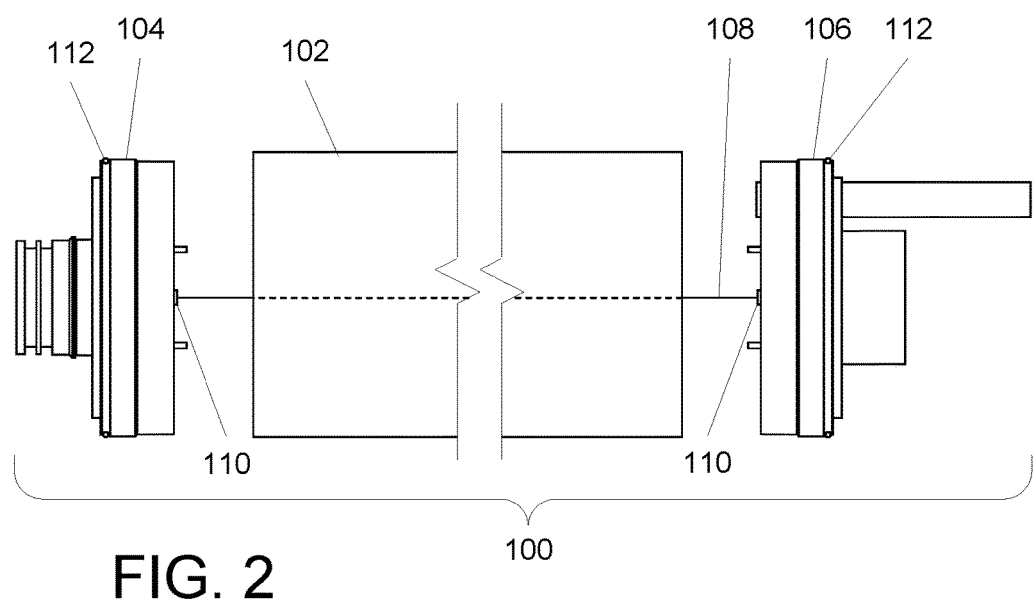
FIG. 2 illustrates, in simplified form, an exploded view of the muon drift tube of FIG. 1.

FIG. 2 illustrates, in simplified form, an exploded view of the muon drift tube 100 of FIG. 1. As shown, the muon drift tube is made up of an aluminum tube 102, two aluminum end caps 104, 106 and a conductive wire 108 that transits the length of the aluminum tube 102. The conductive wire 108 is coupled at either ends to electrodes 110 and, in the assembled muon drift tube 100, the conductive wire 108 is tensioned and co-linear with the longitudinal axis of the aluminum tube 102.

As shown in FIG. 1 and FIG. 2, an aluminum weld ring 112 is attached to each end cap 104, 106 at the location where, post manufacture, the circumferential joint between the aluminum tube 102 and each aluminum end cap 104, 106 will be. Laser welding involving this weld ring 112 is used to form a seal between the respective ends of the aluminum tube 102 and their respective aluminum end caps 104, 106.

Figure 3A:
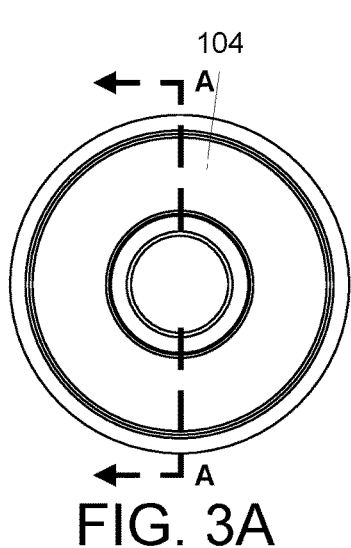
FIGS. 3A-3C respectively illustrate, in simplified form, the end view, side view and a central cross section of the aluminum end cap of FIGS. 1-2 taken at A-A of FIG. 3A.
Figure 3B:
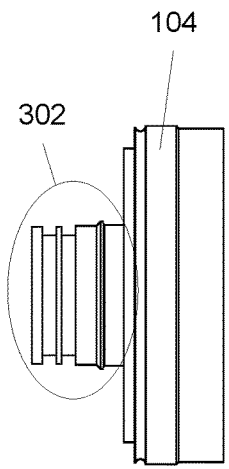
Figure 3C:
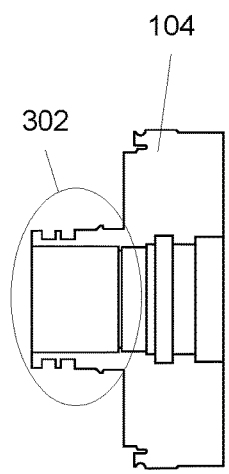

FIGS. 3A-3C respectively illustrate, in simplified form, the end view, side view and a central cross section of the aluminum end cap 104 of FIGS. 1-2 taken at A-A of FIG. 3A.

Figure 4A:
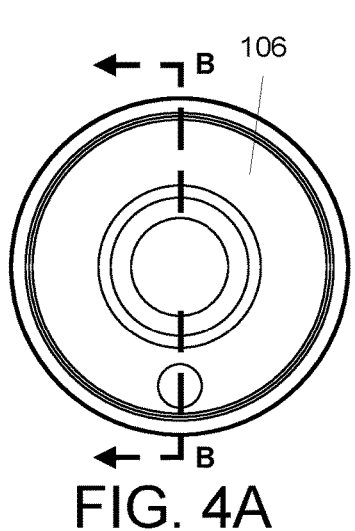
FIGS. 4A-4C respectively illustrate, in simplified form, the end view, side view and a central cross section of the aluminum end cap of FIGS. 1-2 taken at B-B of FIG. 4A.
Figure 4B:
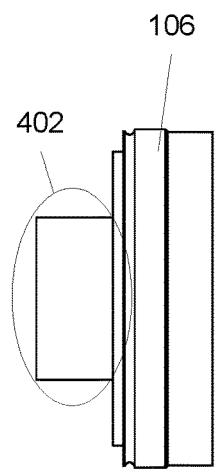
Figure 4C:
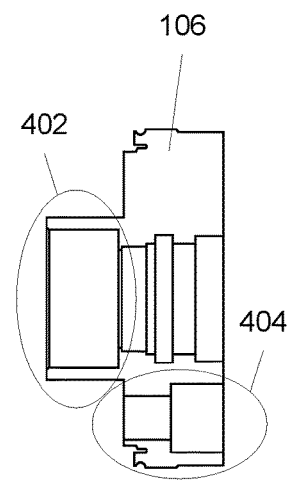

FIGS. 4A-4C respectively illustrate, in simplified form, the end view, side view and a central cross section of the aluminum end cap 104 of FIGS. 1-2 taken at B-B of FIG. 4A.

As shown, the aluminum end cap 104 of FIG. 3C is optionally configured as a "male" end style 302 end cap. In contrast, the aluminum end cap 106 of FIG. 4C is optionally configured as a "female" end style 402 end cap. Advantageously, this male-female configuration allows two muon drift tubes 100 to be connected to each other end-to-end to result in a longer effective length muon drift tube. When this optional approach is used, since the end caps 104, 106 are not capable of detecting muons, it is desirable to have the end caps as short (in a tube-longitudinal direction) as possible.

In addition, the aluminum end cap 106 includes a fill tube opening 404 that can be used to introduce the reactive gas into an assembled muon drift tube 100 and then sealed.

Figure 5:
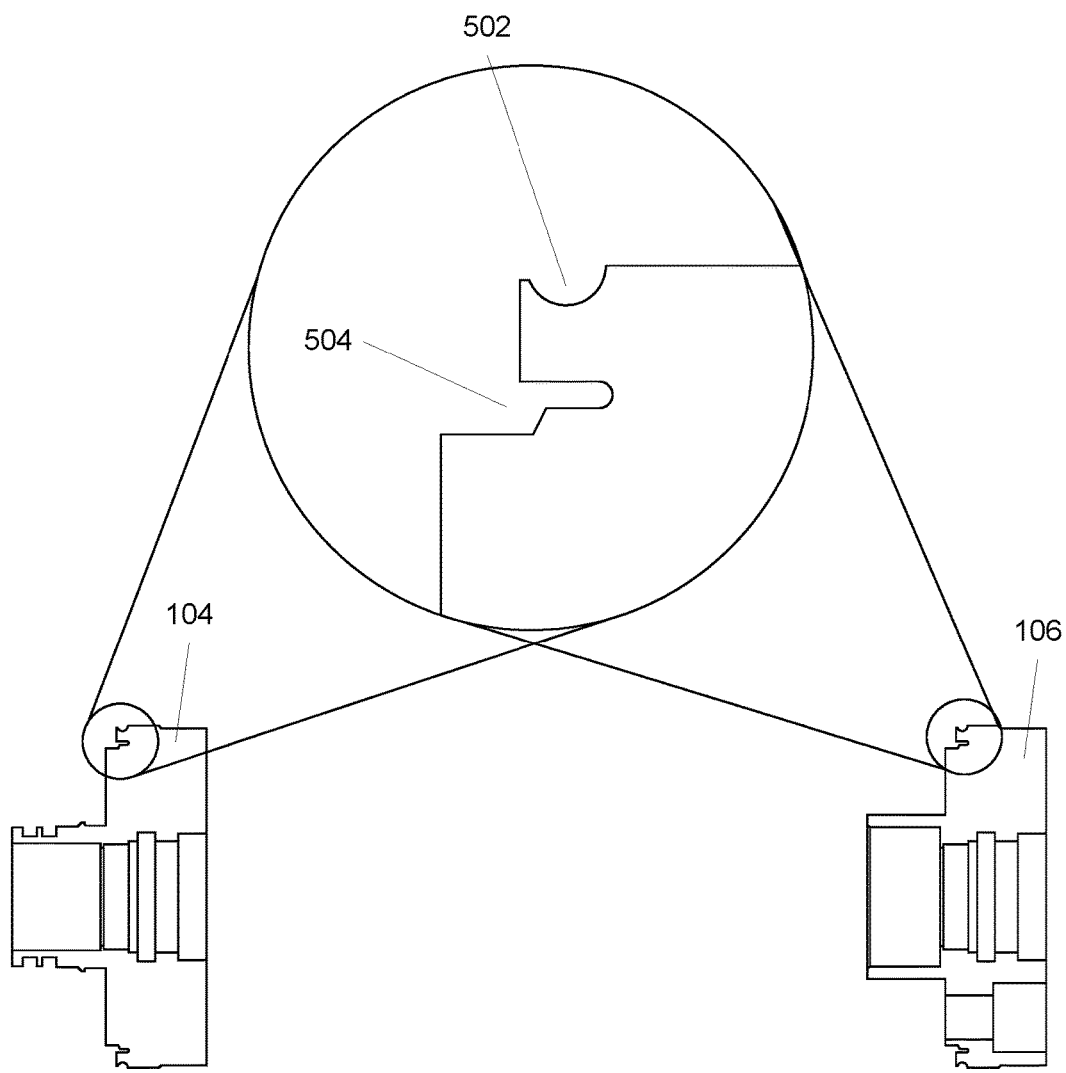
FIG. 5 Illustrates, in simplified form, an enlarged portion of the cross sections of the aluminum end caps of FIG. 3C and FIG. 4C.

FIG. 5 Illustrates, in simplified form, an enlarged portion of the cross sections of the aluminum end caps 104, 106 of FIG. 3C and FIG. 4C. As shown in FIG. 5, and as noted above, in order to ensure that a seal can be created, at manufacture, between the aluminum tube and end caps 104, 106 that will ensure a Helium gas leak rate of less than $1 \times 10^{-8}$ bar l/s, the conventional aluminum end caps require high precision machining of certain features. Specifically, the aluminum end caps 104, 106 require high precision machining of an annular groove 502 that will accept the weld ring 112 of FIGS. 1-2 and other high precision features 504 that are used by the vision system of the high precision laser welding equipment to laser weld an aluminum end cap 104, 106 to the associated tube 102 of FIG. 2

As noted above, the equipment and time involved in creation of those features 502, 504 add significant cost to the manufacture of muon drift tubes 100 and require significant expertise to ensure creation of a proper seal.

What follows is a description of the components and method for construction of a muon drift tube that requires fewer parts, is simpler to manufacture, and does not require all the expensive and complex equipment needed to manufacture a muon drift tube as described in connection with FIGS. 1-5.

FIG. 6A illustrates, in simplified form, an exploded, cross sectional, view of the components of one example variant "female" style end cap 600 for use in constructing a muon drift tube. The end cap 600 includes an aluminum cap body 602, an electrode insulator 604, an electrode 606 to which an anode wire 108 will be coupled, and an end cap insulator 608. The electrode insulator 604 and end cap insulator 608 are used to electrically isolate the electrode 606 from the aluminum cap body 602.

FIG. 6B illustrates, in simplified form, a cross sectional, view of the assembled example variant "female" style end cap 600 of FIG. 6A. As shown in FIG. 6B, a non-conductive epoxy 610 is used to fill post-assembly voids and affix the various components 604, 606, 608 into the aluminum cap body 602.

FIG. 7A illustrates, in simplified form, an exploded, cross sectional, view of the components of an alternative example variant end cap 700 for use in constructing a muon drift tube. The end cap 700 is similar to the end cap of FIGS. 6A-6B except that it is a "male" style and the aluminum cap body 702, and includes a fill tube opening 404 configured to accept a fill tube 704 therein.

FIG. 7B illustrates, in simplified form, a cross sectional, view of the assembled example variant "male" style end cap 700 of FIG. 7A. As shown in FIG. 7B, and similar to FIG. 6B, a non-conductive epoxy 610 is used to fill post-assembly voids and affix the various components 604, 606, 608, 702 into the aluminum cap body 602.

At this point, it should be understood that, as with the conventional end caps 104, 106, the fill tube opening 404 and fill tube 702 could be in either style cap 600, 700, the placement being one of design choice. In addition, it is to be further understood that an end cap as described herein can be constructed that is neither a "male" type nor a "female" type end cap.

FIG. 8 illustrates, in simplified form, a cross sectional, view of an assembled example variant aluminum end cap 800 that is "generic" in that it is neither "male" style nor "female" style. As with the male and female styles, the generic aluminum end cap 800 can optionally include a fill tube opening 404 (shown in dashed lines) if a fill tube is to be attached to that aluminum end cap 800.

Having shown the relevant components, various examples of our simplified approach to joining two pieces of aluminum in a way that is appropriate for constructing a muon drift tube and, more particularly, achieving the requisite gas seal that will ensure a Helium gas leak rate of less than $1\times10^{-8}$ bar l/s, between those two pieces of aluminum, for example, an aluminum tube and aluminum end cap, will now be discussed using different variant aluminum end cap configurations.

As an initial matter, it is to be understood that, although a particular variant may be shown in connection with a male style, a female style or generic style end cap, unless otherwise expressly noted herein, each such connection variant could be used with any other style end cap in addition to, or as alternatives to, the ones described herein.

Figure 9:
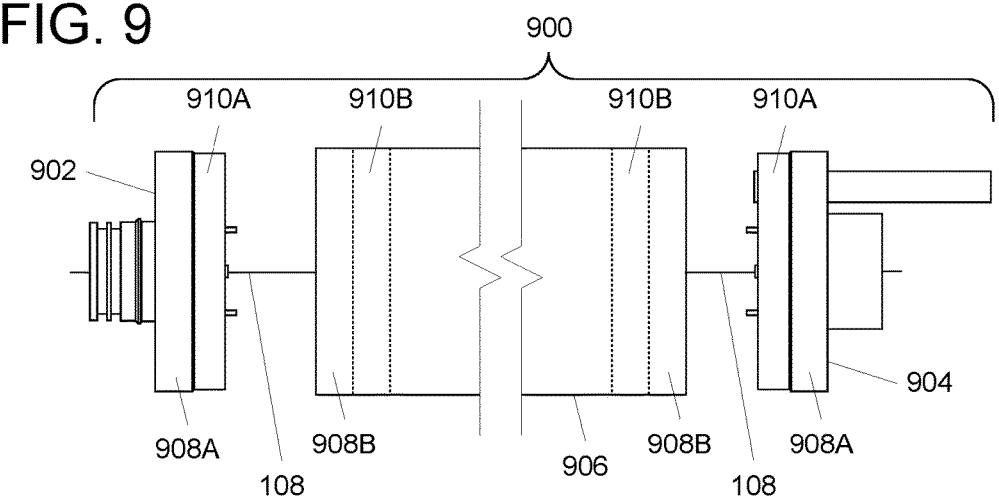

FIG. 9 illustrates, in simplified form, one example variant of our approach to sealing an aluminum end cap 902, 904 to an aluminum tube 906 during formation of a muon drift tube 900 so as to form an electrically conductive, gas-sealed connection between.

As shown in FIG. 9, each of the aluminum end caps 902, 904 include a first segment 908A and a second segment 910A. The aluminum tube correspondingly has a first segment 908B and a second segment 910B with which the respective end cap 902, 904 segments 908A, 910A will be joined during assembly to create the required sealed connection between them without the need for a weld ring or precision machined special features.

Figure 10:
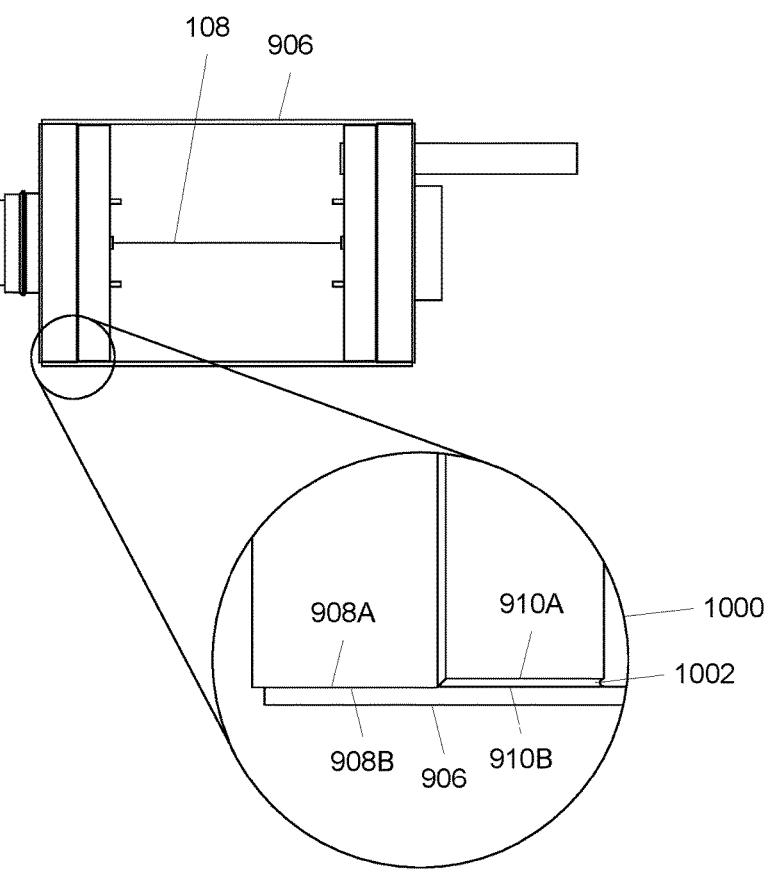
FIG. 10 illustrates, in simplified form, the variant muon drift tube of FIG. 9, as assembled.

FIG. 10 illustrates, in simplified form, the variant muon drift tube 900 of FIG. 9, as assembled, with the aluminum tube 906 shown in cross section to expose part of the sealed connection, which is also shown as an enlarged portion 1000. For purposes of understanding only, the aluminum tube 906 can be considered to have an outer diameter of 5.08 cm (2.0") and a nominal wall thickness of 1.016 mm (0.04"). As also shown, the respective first segments 908A, 908B and second segments 910A, 910B are all roughly equal in length (along the tube longitudinal direction) at about 6.35 mm (0.25"), although this is not a requirement, neither the corresponding segments nor the first and second segments of a component need to be the same length—the only requirement being that the lengths of the corresponding segments are of sufficient lengths so as to perform as intended and described herein.

In order to create an electrically conductive connection, relative motion between two closely spaced aluminum surfaces, under pressure and without lubrication, is used. As shown in the enlarged portion of FIG. 10, merely for purposes of this example, the respective first segments 908A, 908B are configured such that that their diameters only differ by roughly between 0.0254 mm (0.001") and 0.0508 mm (0.002") so that, when the aluminum end cap is inserted into the aluminum tube 906, an interference fit (also referred to as a "press fit") connection will be formed which, as it is being made, causes galling between the surfaces of the two segments 908A, 908B of their respective aluminum components and establish an electrically conductive connection between the aluminum tube 906 and, in this figure, the aluminum end cap 902.

Although specific dimensions in the foregoing paragraph are provided for purposes of explanation and understanding, the spacing needed to create the interference fit will be a straightforward function of lubricity and hardness of the tube and end cap materials, as well as the axial length of the intended interference fit and, in the case of the most common muon tube geometry, a round tube, the outer and/or inner diameter of the tube (depending upon which is used for the interference fit. In general, the fit should be close enough to allow for the relative sliding motion between the two aluminum components while concurrently being close enough to cause sufficient galling between them to create an electrical connection of minimal electrical resitivity appropriate for the intended use.

As is also shown in the enlarged portion of FIG. 10, the respective second segments 910A, 910B are spaced apart, in this example variant, by a radial distance of less than 500 micrometers, but typically greater than 125 micrometers. Within the gap between the second segments 910A, 910B, is a high elongation polymer 1002 that is bonded to the end cap 902 and aluminum tube 906 to form a flexible seal between the two.

In general, high elongation polymers suitable for use as described herein will typically have elongations in the 30% to 500% range, although higher elongations may be acceptable for some applications, with elongations in the 250% to 500% range being contemplated as more typical. Nevertheless, materials with elongations in the range of 100% to 250% can be used for some applications, as can, in some applications, materials with elongations in the 30% to 100% range.

In general, the high elongation polymer to be used will be one that, at a minimum, can be exposed to, in the case of a sealed muon drift tube, the highest operating environment temperature (typically about 55° C.) for normal operational time periods without degradation and should, but need not always, also remain above its glass transition temperature (Tg) at least at the lowest typical operating temperature (typically about −40° C.).

In addition, the high elongation polymer 1002 will typically be a two-part polymer, although the "two part" aspect is not required, that will be applied in precursor form either prior to interference fitting or after the interference fit is formed (the latter being subject to an appropriately selected gap size, high elongation polymer viscosity, and the ability to inject the selected high elongation polymer into the gap post-fitting) and, in either case, that will cure in situ. In the latter case, injecting the high elongation polymer may involve directly introducing it via the open end of the gap, if accessible, or injecting the high elongation polymer into the gap thorough one or more openings provided for that purpose and that will not provide a path for gas within the aluminum tube that bypasses the portion of the seal made up of the interference fit aluminum segments.

Numerous suitable high elongation polymers can be used, depending upon the particular gap spacing. By way of representative, non-limiting, examples, some suitable high elongation polymers include: Epiclon EXA-4816 commercially available from Sun Chemical Corporation, 35 Waterview Boulevard, Parsippany, N.J. 07054, Max Cast A/B commercially available from Polymer Composites Inc., 1871 S. Lake Place, Ontario, Calif. 91761, Epoxonic EX 2840 commercially available from Epoxonic GmbH, Reaktionsharzsysteme, Gewerbestrasse 16, 85652 Landsham/Pliening, Germany, Permabond MT 3809 commercially available from Permabond LLC, 14 Robinson St., Pottstown, Pa. 19464, MasterSil 157 commercially available from Master Bond Inc, 154 Hobart Street, Hackensack, N.J. 07601, TS-33D commercially available from Silicone Solutions, 338 Remington Rd. Cuyahoga Falls, Ohio 44224, 3M 551 commercially available from 3M Company, 3M Center, St. Paul, Minn. 55144, Loctite UK 3173 commercially available from Henkel Corp., 200 Elm Street, Stamford, Conn. 06902, EP21TPND commercially available from Master Bond Inc., 154 Hobart Street, Hackensack, N.J. 07601, PR-1440 commercially available from the PPG Aerospace unit of PPG Industries, Inc., 12780 San Fernando Road, Sylmar, Calif. 91342, and Viton™-containing high elongation polymers such as THA-3000 commercially available from Thermodyn Corp., 3550 Silica Rd., Sylvania, Ohio 43500, and PLV-3145 commercially available from Pelseal Technologies, LLC, 3161 State Road, Ste. G, Bensalem, Pa. 19020.

In general, the selection of the particular high elongation polymer will be a function of the gap spacing, in the axial and/or radial direction, between the corresponding second segments and the viscosity of the particular high elongation polymer. As a guide, a high elongation polymer viscosity in the vicinity of 3,000 centipoise (cP) would be appropriate for a spacing in the range of about 0.0762 mm (0.003") to 0.127 mm (0.005"), whereas a high elongation polymer viscosity in the vicinity of 10,000 cP to 50,000 cP would be more appropriate for a spacing in the range of about 0.254 mm (0.01") to 0.382 mm (0.015"). For a spacing of about 0.508 mm (0.02") high elongation polymer viscosities in the range of 100,000 cP to 1,000,000 cP can be used.

Thus, it should now be generally understood that the connection formed by the segments 908A, 908B, 910A, 910B results in an overall electrically conductive, gas-sealed connection between the aluminum tube and aluminum end cap.

Optionally, for some variants, one or both of the second segments (i.e., of the aluminum tube and/or aluminum end cap) may be surface roughened to promote better adherence of the high elongation polymer to the segments. The surface roughening can be created using any appropriate means, for example, any known mechanical means, such as abrasion or knurling, or any appropriate known chemical means, for example, as disclosed in U.S. Pat. No. 9,493,878, incorporated herein by reference, or any other approach that results in a roughened surface and that does not impede adherence of the selected high elongation polymer.

Now, as shown in the segment configuration of FIG. 9, the second segments 910A, 910B are located on the interior side (gas-containing side) of the tube 906. As a result, with variants using this configuration, the reactive gas will potentially be exposed to cured high elongation polymer during use. In some cases, this may be undesirable due to, for example, the particular gas to be used or the specific high elongation polymer used. Advantageously, for applications where this is the case, alternative configurations are possible that avoid this issue.

Figure 11:
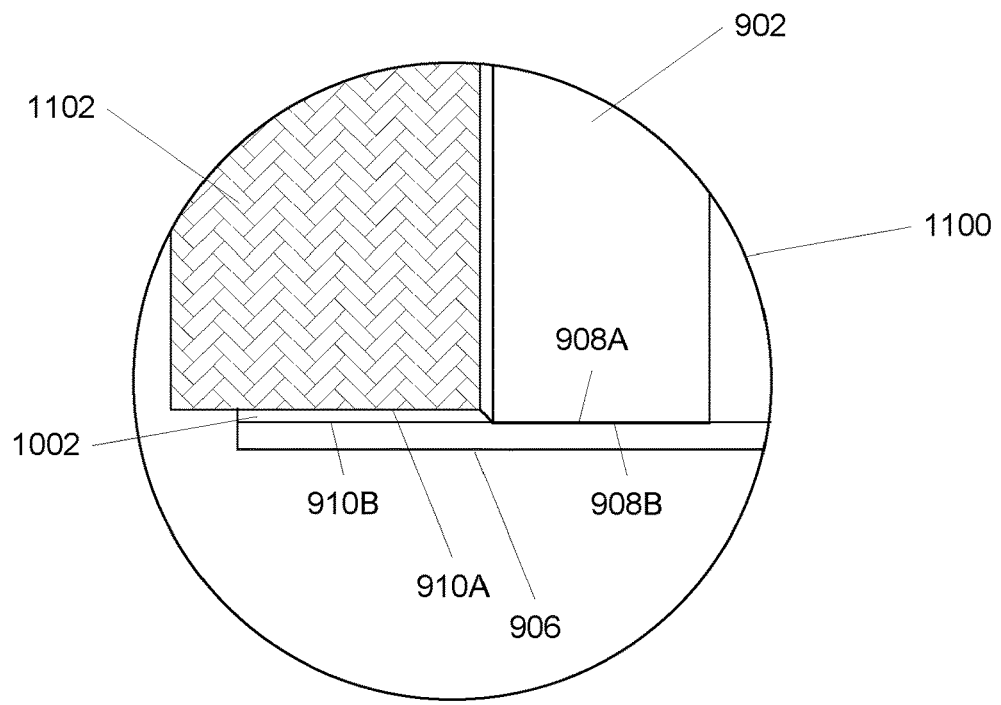
FIG. 11 illustrates, in simplified form, another enlarged cross section cutaway portion of a variant muon drift tube having an electrically conductive, gas-sealed connection that does not result in exposure of the reactive gas to the high elongation polymer.

FIG. 11 illustrates, in simplified form, another enlarged cross section cutaway portion 1100 of a variant muon drift tube having an electrically conductive, gas-sealed connection that does not result in exposure of the reactive gas to the high elongation polymer. Thus, as can be seen, with this configuration, the first segments 908A, 908B are located closer to the tube interior than the second segments 910A, 910B so that, in use, the high elongation polymer 1002 will be separated from the reactive gas by the interference fit formed by the first segments 908A, 908B.

In addition, as represented in FIG. 11 by the herringbone pattern, the surface of the second segment 910 A of the aluminum end cap 902 has been roughened 1102 to improve adherence of the high elongation polymer 1002 to the aluminum end cap 904 surface.

Figure 12:
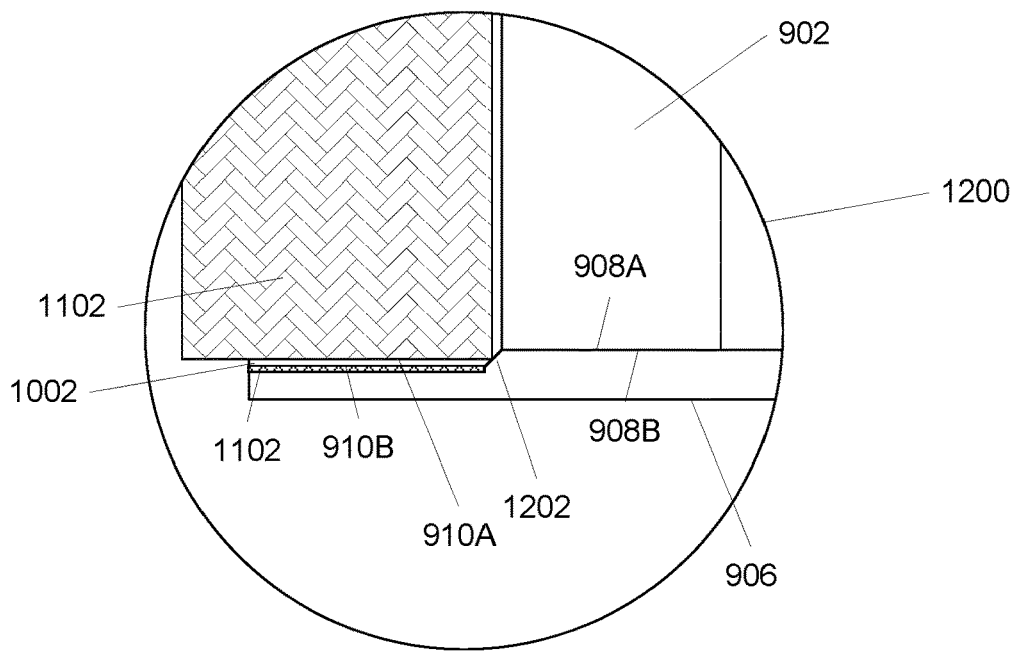
FIG. 12 illustrates, in simplified form, another enlarged cross section cutaway portion of another variant muon drift tube having an electrically conductive, gas-sealed connection that is similar to the variant muon drift tube of FIG. 11.

FIG. 12 illustrates, in simplified form, another enlarged cross section cutaway portion 1200 of another variant muon drift tube having an electrically conductive, gas-sealed connection that is similar to the variant muon drift tube of FIG. 11, except that the surface of the second segment 910B of the aluminum tube 906 also has a roughened surface 1102 and the inner diameter of the aluminum tube 906 is smaller at the first segment 908B than at the second segment 910B resulting in a "step: or "transition" 1202 between the two. Advantageously, this configuration allows the "step: or "transition" 1202 to serve as a limit on the insertion depth.

Figure 13:
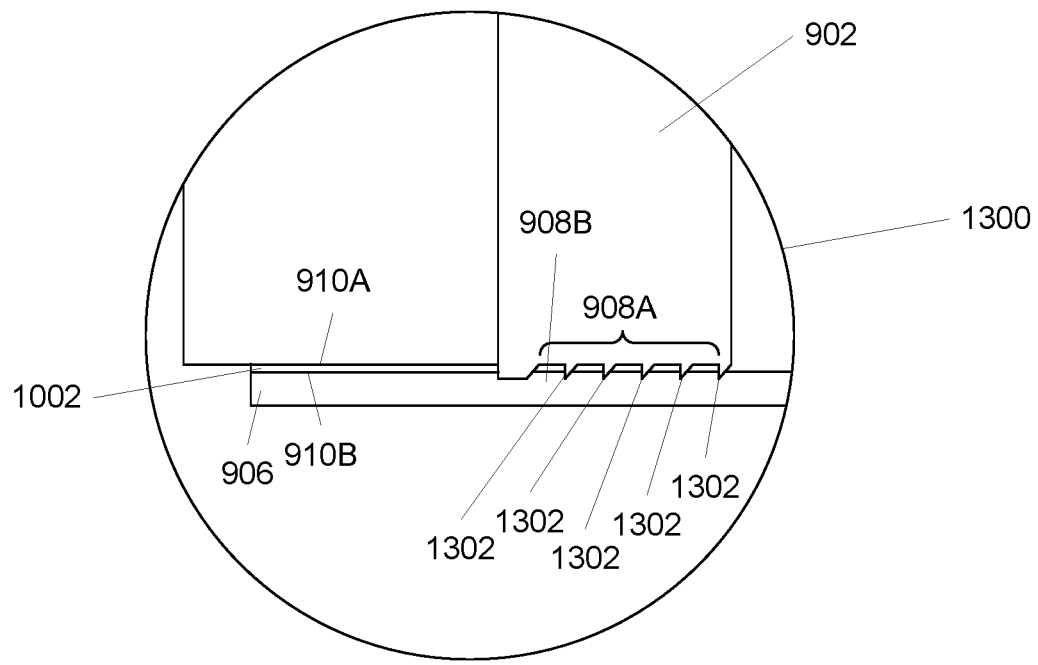
FIG. 13 illustrates, in simplified form, another enlarged cross section cutaway portion of another alternative variant muon drift tube having an electrically conductive, gas-sealed connection between an aluminum end cap and aluminum tube.

FIG. 13 illustrates, in simplified form, another enlarged cross section cutaway portion 1300 of another alternative variant muon drift tube having an electrically conductive, gas-sealed connection between an aluminum end cap and aluminum tube.

As shown in FIG. 13, this variant, is similar to FIG. 11 and FIG. 12 with respect to the second segments 910A, 910B and the first segment 910B of the aluminum tube. However, the first segment of the aluminum end cap 902 of this variant includes one or more annular or helical protrusions 1302, depending upon the particular implementation, that form the interference fit with the tube 906 and establish the electrically conductive connection between the aluminum end cap 902 and aluminum tube 906.

Figure 14:
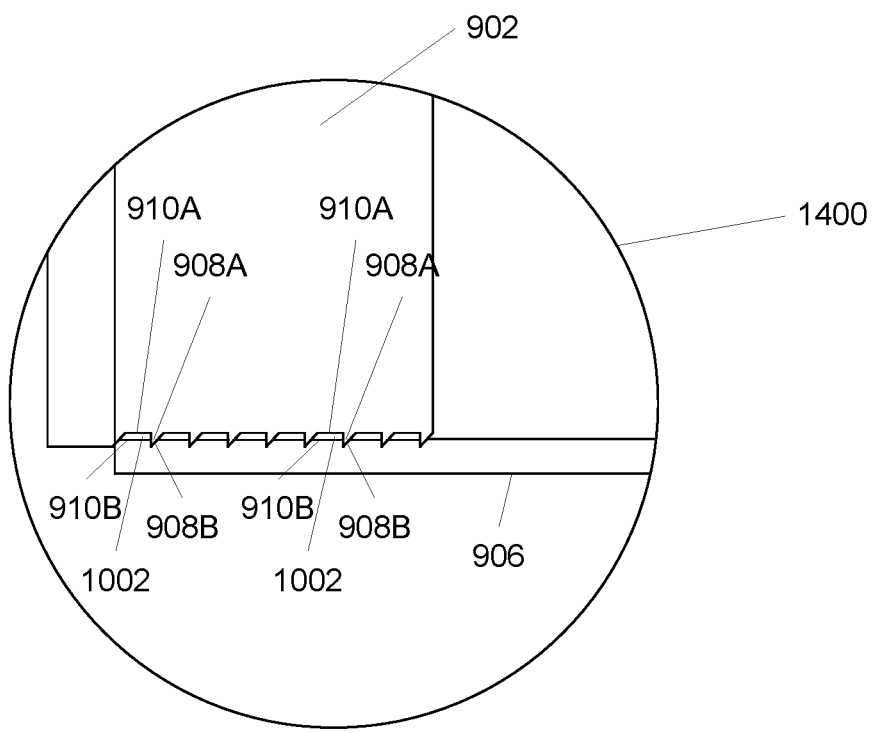
FIG. 14 illustrates, in simplified form, an additional enlarged cross section cutaway portion of yet another alternative variant muon drift tube having an electrically conductive, gas-sealed connection between an aluminum end cap and aluminum tube.

FIG. 14 illustrates, in simplified form, an additional enlarged cross section cutaway portion 1400 of yet another alternative variant muon drift tube having an electrically conductive, gas-sealed connection between an aluminum end cap and aluminum tube.

The variant of FIG. 14 is, in effect, a hybridization of the prior-described variants in that the surfaces of the annular or helical protrusions 1302 that intrude into the surface of the aluminum tube 906 collectively comprise the first segment 908A of the aluminum end cap 902 and the corresponding surfaces of the aluminum tube 906 collectively comprise the first segment 908B of the aluminum tube 906. In addition, the gap(s) between the annular or helical protrusions 1302 are where the high elongation polymer 1002 is located. For clarity, only a few instances of the segments 908A, 908B, 910A, 910B and high elongation polymer 1002 have been indicated.

Advantageously, for some implementations employing the teachings of FIG. 13 and/or FIG. 14, involving one or more protrusions 1302 that are specifically helical, the presence of those helical protrusions 1302 can allow for the interference fit to be created by relative rotation between the aluminum end cap and aluminum tube, in the manner of tightening a bolt or screw.

A further advantage arising from some implementations according to the teachings of FIG. 14 is that a "shorter" end cap can be created due to the interleaving or combining of the first and second segments 908A, 908B, 910A, 910B.

FIG. 15 illustrates, in simplified form, an additional enlarged cross section cutaway portion 1500 of yet another alternative variant muon drift tube having an electrically conductive, gas-sealed connection between an aluminum end cap and aluminum tube.

As shown in FIG. 15, a portion of the inner diameter surface 1502 of the aluminum tube 906 has been removed to create a surface 1504 at an enlarged diameter. As a result, with this variant, the high elongation polymer 1002 can be inserted into the differential volume between the two surfaces 1502, 1504. By doing so, an end cap with helical protrusions can be "screwed" into the tube, such that the protrusions will cut through the high elongation polymer 1002 and form the electrically conductive connection between the protrusions and tube 906.

FIG. 16A illustrates, in simplified form, a cross section of a further alternative variant aluminum end cap 1600 for use in constructing a muon drift tube having an electrically conductive, gas-sealed connection between an aluminum end cap and aluminum tube.

FIG. 16B illustrates, in simplified form, a cross section of the aluminum end cap 1600 taken at C-C as it would look after insertion into an aluminum tube 906.

As shown in FIGS. 16A-16B, this aluminum end cap 1600 is a variation on the end cap 904 of FIG. 15 except that part of the first segment includes alternative protrusions that, in some implementation variants, extend in the tube-axial direction, in the manner of the teeth of a spur gear relative to its axle, or, in other variants, the alternative protrusions continually offset as one looks along the tube axial direction, in the manner of the teeth of a helical gear relative to its axle. With this implementation variant, as with some other protrusion variants, the high elongation polymer 1002 can be placed between the protrusions before insertion into the tube 902, or the high elongation polymer 1002 can be present on the tube 906, in the manner described in connection with FIG. 15, prior to insertion of the aluminum end cap 1600.

Up until now, the foregoing variant examples have been described in connection with an aluminum end cap that interference fits inside of an aluminum tube. It should also be understood that implementations can be constructed that are the reverse, in that the connection aspects described in connection with the aluminum end cap, e.g., features like roughening, protrusion, high-elongation polymer placement, etc, could be present on the aluminum tube instead and the connection aspects described in connection with the aluminum tube could be present on the aluminum end cap instead. In addition, in some variants, the connection aspects, e.g., features like surface roughening, protrusion placement, high-elongation polymer placement, etc, could be on both the aluminum tube and aluminum end cap.

Likewise, it should be understood that same approaches can be used for variants where an aluminum tube fits inside of an aluminum end cap, or an aluminum end cap surrounds an aluminum tube.

Figure 17A:
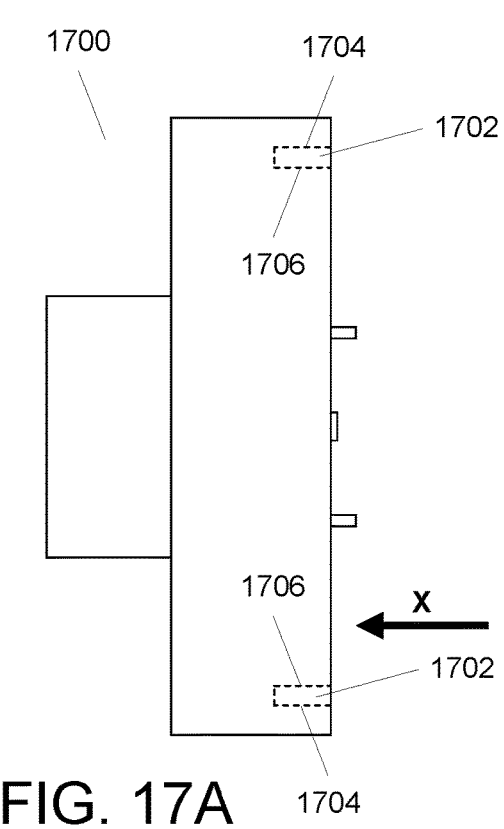
FIG. 17A illustrates, in simplified form, an additional variant aluminum end cap for use according to the teachings herein to form an electrically conductive, gas-sealed connection between an aluminum end cap and an aluminum tube.

FIG. 17A illustrates, in simplified form, an additional variant aluminum end cap 1700 for use according to the teachings herein to form an electrically conductive, gas-sealed connection between an aluminum end cap and an aluminum tube. As shown, the aluminum end cap 1700 includes an annular groove 1702 within the aluminum end cap 1700 that is located and dimensioned to receive an aluminum tube therein. Depending upon the particular implementation, the outer circumferential surface 1704 of the groove 1702 can be dimensioned such that it will be the surface that forms all or part of an interference fit with a corresponding aluminum tube. Alternatively, the inner circumferential surface 1706 of the groove 1702 can be dimensioned such that it will be the surface that forms all or part of an interference fit with a corresponding aluminum tube.

Likewise, where the outer circumferential surface 1704 of the groove 1702 forms all or part the interference fit with an aluminum tube, a) another portion of that surface 1704 can be the segment where the high elongation polymer will be located, and/or b) the inner circumferential surface 1706 of the groove 1702 can be all or part of the surface where high elongation polymer will be located.

Conversely, where the inner circumferential surface 1706 of the groove 1702 forms all or part the interference fit with an aluminum tube, a) another portion of that surface 1706 can be the segment where the high elongation polymer will be located, and/or b) the outer circumferential surface 1704 of the groove 1702 can be all or part of the surface where high elongation polymer will be located.

Figure 17B:
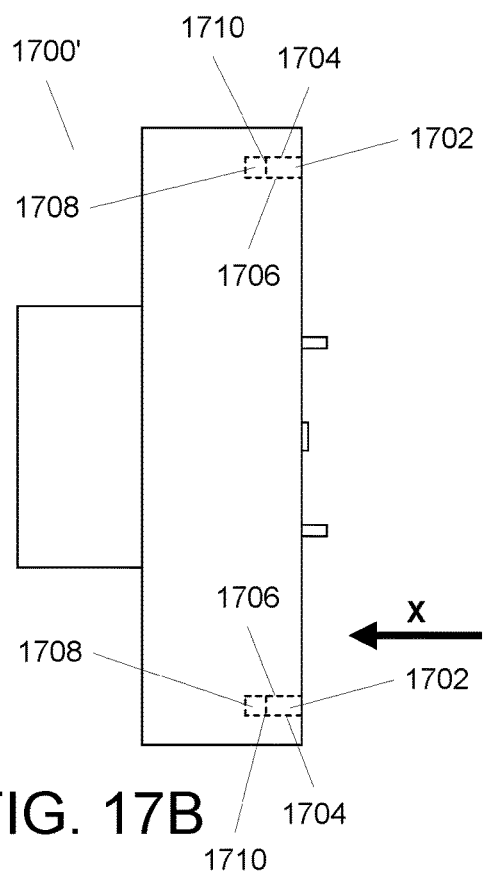
FIG. 17B illustrates, in simplified form, a modified further variant of the aluminum end cap of FIG. 17A.

FIG. 17B illustrates, in simplified form, a modified further variant 1700' of the aluminum end cap 1700 of FIG. 17A. With the variant end cap 1700' of FIG. 17B, the groove 1702 is deeper than the portion of the aluminum tube that will be inserted therein. With this variant, the added depth 1708 allows for insertion of high elongation polymer therein instead of, or in addition to, the configurations described in connection with FIG. 17A. Depending upon the particular implementation, the presence of high elongation polymer in the deepest part of the groove 1702 can itself serve as a form of insertion depth limit or a depth limiting feature 1710, for example a step or diameter change can effect the same result.

Figure 17C:
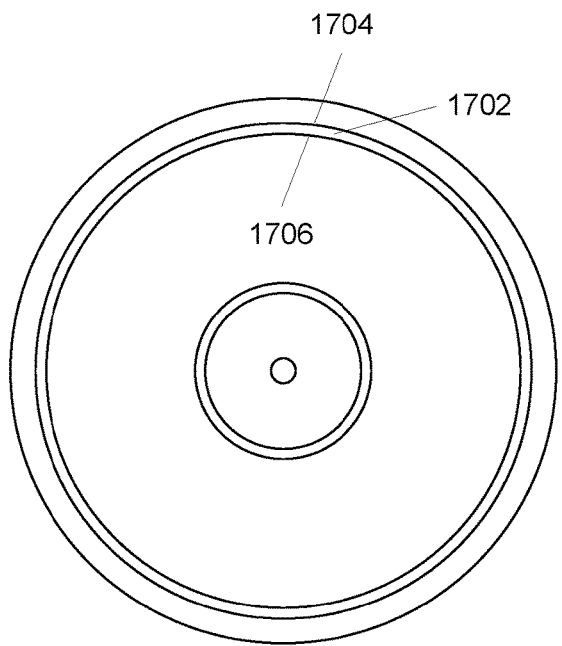
FIG. 17C illustrates, in simplified form, an end view of the aluminum end caps of FIG. 17A or FIG. 17B.

FIG. 17C illustrates, in simplified form, an end view of the aluminum end caps 1700, 1700' of FIG. 17A or FIG. 17B viewed in the direction of the arrow "X" in those figures.

Figure 18A:
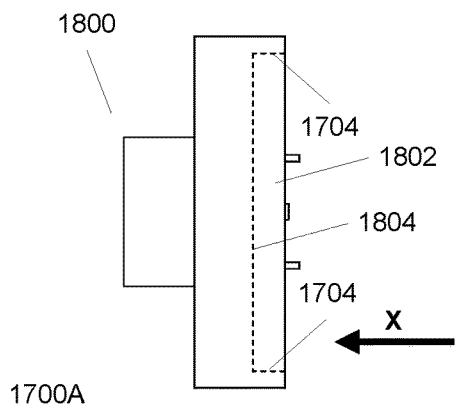
FIG. 18A illustrates, in simplified form, a further alternative variant aluminum end cap suitable for use in forming an electrically conductive, gas-sealed connection between an aluminum end cap and an aluminum tube according to the teachings herein.

FIG. 18A illustrates, in simplified form, a further alternative variant aluminum end cap 1800 suitable for use in forming an electrically conductive, gas-sealed connection between an aluminum end cap and an aluminum tube according to the teachings herein. As shown, the aluminum end cap 1800 of FIG. 18A is similar to the aluminum end caps 1700, 1700' of FIG. 17A and FIG. 17B except that, instead of a narrow groove, the aluminum end cap 1800 contains a circumferential recess 1802 that, with respect to creating an electrically conductive, gas-sealed connection to an aluminum tube, forms the surface 1704 of FIG. 17A or FIG. 17B. Depending upon the particular implementation, any of the foregoing cap-in-tube connection approaches can be used or, if desired, and the depth 1804 of the recess 1802 is greater than the intended tube-insertion depth, an approach like that of FIG. 17B can be used to form the electrically conductive, gas-sealed connection to an aluminum tube.

Figure 18B:
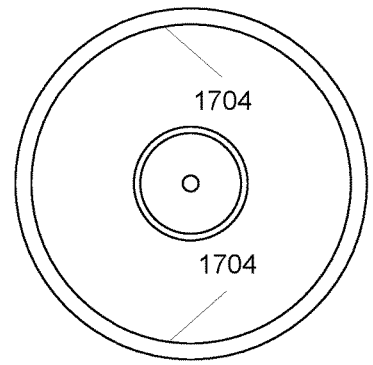
FIG. 18B illustrates an end view of the aluminum end cap of FIG. 18A.

FIG. 18B illustrates an end view of the aluminum end cap 1800 of FIG. 18A viewed in the direction of the arrow "X" in FIG. 18A.

Figure 19:
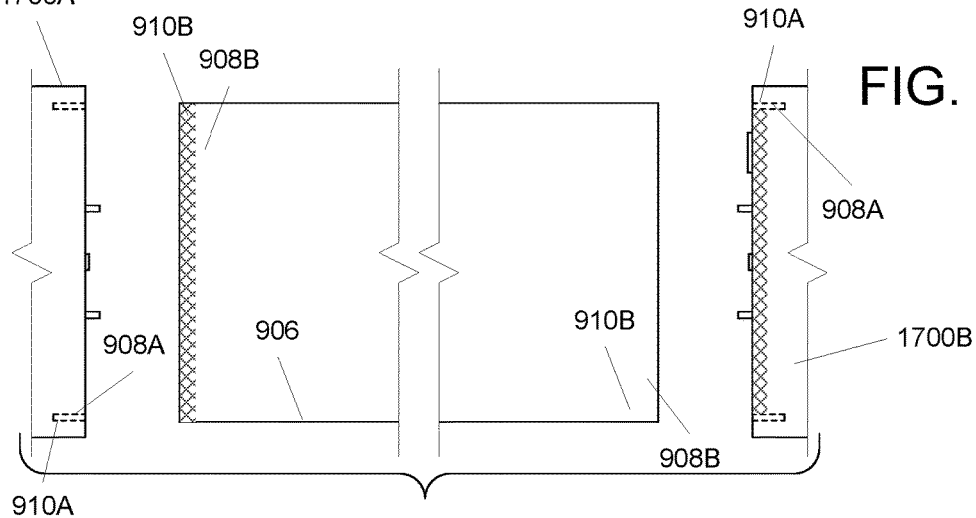
FIG. 19 illustrates, in simplified form, portions components of a muon drift tube, prior to connection, and employing end caps constructed according the teachings of FIG. 17A or FIG. 17B or 18A.

FIG. 19 illustrates, in simplified form, portions components of a muon drift tube, prior to connection, and employing end caps 1700A, 1700B constructed according the teachings of FIG. 17A or FIG. 17B or 18A in order to form an electrically conductive, gas-sealed connection between the outer surface of the aluminum tube 906 and the surface 1704 of the aluminum end cap 1700A, 1700B using segments 908A, 908B, 910A, 910B as described above.

In addition, as represented in FIG. 19 by cross hatching, the segment 910B on the left end of the tube 906 has been roughened, whereas the aluminum end cap 1700B that will engage the right end of the aluminum tube 906 has been roughened.

Moreover, as can be seen in FIG. 19, for purposes of illustration only, the interference fit segments 908A, 908B the left side of that figure are adjacent to the volume of the tube where the reactive gas will be, whereas, on the right side of that figure, the interference fit segments 908A, 908B are separated from the volume of the tube where the reactive gas will be by the segments 910A, 910B where the high elongation polymer will be located.

Figure 20:
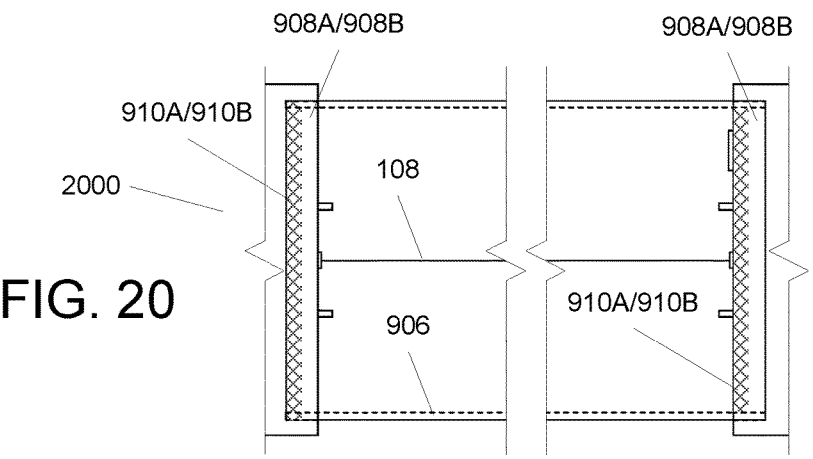
FIG. 20 illustrates, in simplified form, portions of a muon drift tube constructed using the aluminum end caps and aluminum tube of FIG. 19 so as to have an electrically conductive, gas-sealed connection between those aluminum end caps and the aluminum tube.

FIG. 20 illustrates, in simplified form, portions of a muon drift tube 2000 constructed using the aluminum end caps 1700A, 1700B and aluminum tube 906 of FIG. 19 so as to have an electrically conductive, gas-sealed connection between those aluminum end caps and the aluminum tube.

FIG. 21 illustrates, in simplified form, alternative end portions of a muon drift tube 2100 constructed according to the teachings herein in order to form an electrically conductive, gas-sealed connection between an aluminum end cap and aluminum tube using an end cap having a groove 1702 as described in connection with FIG. 17A with part of the connections between the aluminum end caps and aluminum tube shown in enlarged cross section.

As shown in FIG. 21, the aluminum end cap 2102 on the left side of the figure is coupled to the aluminum tube 906 such that the first segments 908A, 908B that are interference fit are on the interior surface of the tube 906 and abut the smaller diameter surface of the groove, whereas the second segments 910A, 910B are on the exterior surface of the tube 906 with the high elongation polymer 1002 located in between.

In contrast, the aluminum end cap 2104 on the right side of the figure is coupled to the aluminum tube 906 such that the first segments 908A, 908B that are interference fit are on the exterior surface of the tube 906 and abut the larger diameter surface of the groove, whereas the second segments 910A, 910B are on the interior surface of the tube 906 with the high elongation polymer 1002 located in between.

FIG. 22 illustrates, in simplified form, enlargements of cross sections of alternative end portions of a muon drift tube 2200 (only part of which is shown) that was constructed according to the teachings herein in order to form an electrically conductive, gas-sealed connection between an aluminum end cap and aluminum tube, using an end cap having a groove 1702 as described in connection with FIG. 17B.

As shown in enlarged view alternative "A" of FIG. 22, the aluminum end cap 2202 has two first segments 908A, located on both the larger diameter and smaller diameter surfaces of the groove 1702. Likewise, the aluminum tube 906 has two first segments 908B on both its exterior and interior surfaces.

In contrast, with this variant configuration, the terminal end 2204 of the aluminum tube 906 forms the second segment 901B of the aluminum tube 906 and the second segment 910A of the aluminum end cap includes the deepest part of the groove 1702 along with the sections of the larger and smaller diameter surfaces of the groove 1702 that are beyond the terminal end 2204 of the aluminum tube 906, such that the high elongation polymer 1002 (indicated using diagonal hashing) will be located in between.

Enlarged view alternative "B" of FIG. 22, is a hybrid combination of alternative "A" and the upper expanded view of FIG. 21. Thus, with alternative "B", the first sections 908A, 908B are only located on the exterior side of the tube 906 and surface of the larger diameter surface of the groove 1702, and the second sections 910A, 910B are both beyond the terminal end 2204 of the tube 906 and on the interior surface of the tube 906 and smaller diameter surface of the groove 1702.

Enlarged view alternative "C" of FIG. 22, is a hybrid combination of alternative "A" and the lower expanded view of FIG. 21. Thus, with alternative "C", the first sections 908A, 908B are only located on the interior side of the tube 906 and surface of the smaller diameter surface of the groove 1702, and the second sections 910A, 910B are both beyond the terminal end 2204 of the tube 906 and on the exterior surface of the tube 906 and larger diameter surface of the groove 1702.

As noted previously, configurations similar to FIG. 21 and/or FIG. 22 can also include features such as roughening and/or protrusions.

Having described numerous variant components that can be used to make a muon drift tube that includes an electrically conductive, gas-sealed connection between an aluminum end cap and the aluminum tube, an example of method for making a muon drift tube according to the teachings herein will now be described.

The method involves:
i) threading an anode wire through an aluminum tube having a first end, a second end, and a longitudinal axis, such that the wire extends beyond both the first end and second end of the aluminum tube,
ii) inserting a first end of the anode wire into a first electrode located within, but electrically isolated from, a first end cap; and
iii) inserting a second end of the anode wire into a second electrode located within, but electrically isolated from, a second end cap.

Steps "i)," "ii)" and "iii)" can occur in any order, provided that steps "ii)" and "iii)" cannot likely both occur prior to step "i)" for most implementations.

The method then involves, in one variant approach, at some point, before, concurrent with, or following completion of, any one or more of steps "i)"-"iii)" but before coupling of the specific part to which the high elongation polymer will be applied, applying a high elongation polymer, as described herein (selected consistent with the gap in which it will be used) to a second segment of at least one of the first part of the first end cap, or a second segment of the first end of the aluminum tube, while ensuring that a first segment of both the first part of the first end cap and a first segment of the second end of the aluminum tube is substantially free of the high elongation polymer. This may be performed by applying the high elongation polymer to only select portions of the appropriate component(s) or by more broadly applying the high elongation polymer and then removing some of the applied high elongation polymer that need to be substantially free of the high elongation polymer, for example, to ensure a good electrically conductive connection can be formed. Note here that "substantially free" as used herein is intended to mean that there can be some minor residual high elongation polymer in the areas that are intended to be free of the high elongation polymer, resulting from the application process or that may occur during joining of components, the important aspect being that whatever high elongation polymer is present, it is not present in a sufficient amount or over a sufficient area such that the desired electrically conductive connection cannot or will not be formed. Alternatively, with the appropriately selected gap spacing and high elongation polymer, this step can be delayed until after the aluminum end cap and aluminum tube are joined.

The method then involves, for the variants where the high elongation polymer is applied prior to joining:
iv) coupling a first part of the first end cap to the first end of the aluminum tube and coupling a first part of the second end cap to the second end of the aluminum tube, (bearing in mind that application of the high elongation polymer must occur before the particular part is coupled in this step). This coupling of the first part of an end cap to an end of the aluminum tube comprises interference fitting the first part of the first end cap and the first end of the aluminum tube together such that galling will occur between the respective first segments and a flexible seal will be formed by the high elongation polymer located between the respective second segments, such that the first and second segments collectively form an electrically conductive, gas-sealed, connection between the first end cap and the aluminum tube.

For variant approaches where the high elongation polymer is not applied prior to coupling a first part of the first end cap to the first end of the aluminum tube and/or coupling a first part of the second end cap to the second end of the aluminum tube, once the coupling of an end cap to an end of the aluminum tube is complete, at any time thereafter, but prior to insertion of the reactive gas, the high elongation polymer will be injected into the gap and cured to form the flexible seal.

Next, the method involves, depending upon approach variant, either before or after creating the seal with the high elongation polymer, "v)" tensioning the anode wire such that the longitudinal axis of the aluminum tube and the anode wire are co-linear; and, finally "vi)" coupling portions of the tensioned anode wire, associated with the first and second ends of the tensioned anode wire, to the first and second electrodes.

While this is just one simplified example of how to make a muon drift tube according to the teachings herein, any other method of making a muon drift tube, including conventional methods, that can be straightforwardly modified to be compatible with, and/or accommodate, the configuration variants described herein can be used.

It is to be noted and understood that although certain geometries have been illustrated for the various tubes, end caps, grooves, protrusions, limiting features, etc., those were provided merely for purposes of illustration and understanding, and that numerous other variations and modifications of those aspects, by way of non-limiting example, rounded as opposed to squared corners or vice versa, different size, number or shaped protrusions, filleting, tapering, smooth or abrupt transitions, use of tube shapes other than round, etc. can be straightforwardly incorporated without departing from the teachings herein, the permutations and combinations of those variations being straightforwardly usable by one of ordinary skill in light of the teachings herein. Moreover, roughening can be used on the segments that form the interference fit connection, provided that the connection made does not have an undesirably high resistivity for the intended application.

It is also to be noted and understood that, merely for purposes of illustration, in some figures and the associated description, the end cap connections to the tube are shown as using different variants at opposite ends. In reality, while the use of two different variants of end cap to tube connections could be used on different ends of a given tube to construct a muon drift tube, in practice, in many implementation cases, the same connection style will be used on both ends. Thus, it should be understood that the use of the same variant style of connection on both ends of the tube and different variant styles on opposite ends of the tube are all contemplated. Moreover, it is contemplated that, in some cases, a connection variant consistent with the teachings herein may be used on one end of a muon drift tube, while an opposite end may incorporate a conventional connection between the end cap and tube. Thus, the description herein should not be considered as requiring any particular muon drift tube to have more than one end cap-to-tube coupling constructed consistent with the teachings herein.

Finally, while the foregoing description has focused specifically on joining an end cap to a tube, the same approaches can be used to join two aluminum tubes together using a sleeve coupling in place of the end cap where both electrical conductivity and a gas seal as described herein is desired, for example, to create a longer muon drift tube.

Having described and illustrated the principles of this application by reference to one or more examples, it should be apparent that the embodiment(s) may be modified in arrangement and detail without departing from the principles disclosed herein and that it is intended that the application be construed as including all such modifications and variations insofar as they come within the spirit and scope of the subject matter disclosed.

What is claimed is:

1. A muon drift tube for use in muon tomography comprising:
   an aluminum tube having a first end, a second end, and a longitudinal axis;
   an aluminum first cap coupled to the first end of the tube;
   an aluminum second cap coupled to the second end of the tube;
   a first electrode physically coupled to, but electrically isolated from, the first cap;
   a second electrode physically coupled to, but electrically isolated from, the second cap;
   a conductive wire within the tube extending, along the longitudinal axis, between the first electrode and the second electrode,
   wherein the first cap and the first end of the tube are coupled to each other so as to form an electrically conductive, gas-sealed connection between them, the connection including
     a) interference-fit-based galling between a first segment of the first end of the aluminum tube and a corresponding first segment of the first cap, and
     b) a high elongation polymer, having an elongation of 30% or greater, located between a second segment of the aluminum tube and a corresponding second segment of the first cap; and
   wherein a thickness of the high elongation polymer, measured radially normal to a surface of the tube at the second segment of the connection, is less than 500 micrometers.

2. The muon drift tube of claim 1, wherein the connection comprises:
   the segments being located so that the first segments are located between the second segments and an interior volume defined by an interior wall of the aluminum tube.

3. The muon drift tube of claim 1, wherein the connection comprises:
   the segments being located so that the second segments are located between the first segments and an interior volume defined by an interior wall of the aluminum tube.

4. The muon drift tube of claim 1, wherein at least one of the first segments includes at least one protrusion.

5. The muon drift tube of claim 1, wherein at least one of the first segments is located on an interior wall of the aluminum tube.

6. The muon drift tube of claim 1, wherein at least one of the first segments is located on an exterior wall of the aluminum tube.

7. The muon drift tube of claim 1, wherein at least one of the second segments is located on an interior wall of the aluminum tube.

8. The muon drift tube of claim 1, wherein at least one of the second segments is located on an exterior wall of the aluminum tube.

9. The muon drift tube of claim 1, wherein the second segment of the aluminum tube includes a terminal end surface of the aluminum tube.

10. A muon drift tube for use in muon tomography comprising:
    an aluminum tube having a first end, a second end, and a longitudinal axis;
    an aluminum first cap coupled to the first end of the tube;

an aluminum second cap coupled to the second end of the tube;

a first electrode physically coupled to, but electrically isolated from, the first cap;

a second electrode physically coupled to, but electrically isolated from, the second cap;

a conductive wire within the tube extending, along the longitudinal axis, between the first electrode and the second electrode, wherein a first segment of the first end of the aluminum tube and a first segment of the first cap are interference-fit together so as to form an electrically conductive path between them;

wherein a second segment of the first end of the aluminum tube and a corresponding second segment of the first cap are spaced apart from each other so as to form a gap between them of greater than 76.2 micrometers; and a high elongation polymer, having an elongation of 30% or greater, bonded to at least one of the aluminum tube or first cap, and located within the gap, so that, the first segments and second segments will collectively form an electrically conductive, gas-sealed, connection between the first end cap and the aluminum tube.

11. The muon drift tube of claim 10, wherein the gap is less than 500 micrometers when measured in an radial direction.

12. The muon drift tube of claim 11, wherein the connection comprises:

the segments being located so that the first segments are located between the second segments and an interior volume defined by an interior wall of the aluminum tube.

13. The muon drift tube of claim 11, wherein the connection comprises:

the segments being located so that the second segments are located between the first segments and an interior volume defined by an interior wall of the aluminum tube.

14. The muon drift tube of claim 11, wherein at least one of the first segments includes at least one protrusion.

15. The muon drift tube of claim 11, wherein at least one of the first segments is located on an interior wall of the aluminum tube.

16. The muon drift tube of claim 11, wherein at least one of the first segments is located on an exterior wall of the aluminum tube.

17. The muon drift tube of claim 11, wherein at least one of the second segments is located on an interior wall of the aluminum tube.

18. The muon drift tube of claim 11, wherein at least one of the second segments is located on an exterior wall of the aluminum tube.

19. The muon drift tube of claim 11, wherein the second segment of the aluminum tube includes a terminal end surface of the aluminum tube.

20. A method of making a muon drift tube for use in muon tomography, the method comprising:

i) threading an anode wire through an aluminum tube having a first end, a second end, and a longitudinal axis, such that the wire extends beyond both the first end and second end of the aluminum tube;

ii) inserting a first end of the anode wire into a first electrode located within, but electrically isolated from, a first end cap;

iii) inserting a second end of the anode wire into a second electrode located within, but electrically isolated from, a second end cap;

iv) coupling a first part of the first end cap to the first end of the aluminum tube, and coupling a first part of the second end cap to the second end of the aluminum tube;

v) tensioning the anode wire such that the longitudinal axis of the aluminum tube and the anode wire are co-linear;

vi) coupling portions of the tensioned anode wire, associated with the first and second ends of the tensioned anode wire, to the first and second electrodes;

wherein, with respect to coupling the first end cap to the aluminum tube, a second segment of one of the first part of the first end cap, or a second segment of the first end of the aluminum tube, includes a high elongation polymer, having an elongation of 30% or greater, and a first segment of both the first part of the first end cap and a first segment of the second end of the aluminum tube are substantially free of the high elongation polymer;

wherein the coupling of the first part of the first end cap to the one end of the aluminum tube in "iv)" comprises interference fitting the first part of the first end cap and the first end of the aluminum tube together such that galling will occur between the respective first segments and wherein the method further includes, forming a flexible seal between the respective second segments, such that the first and second segments collectively form an electrically conductive, gas-sealed, connection between the first end cap and the aluminum tube.

21. The method of claim 20 further comprising, prior to "iv)":

roughening at least one of:

a) the second segment of the first end cap, or b) the second segment of the first end of the aluminum tube.

* * * * *